(12) United States Patent  (10) Patent No.: US 8,167,230 B2
McLawhorn  (45) Date of Patent: May 1, 2012

(54) ENDOSCOPIC SHEET ROLLING SYSTEM

(75) Inventor: Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 249 days.

(21) Appl. No.: 12/635,311

(22) Filed: Dec. 10, 2009

(65) Prior Publication Data

US 2010/0147990 A1  Jun. 17, 2010

Related U.S. Application Data

(60) Provisional application No. 61/121,794, filed on Dec. 11, 2008.

(51) Int. Cl.
B65H 75/18 (2006.01)
(52) U.S. Cl. ............ 242/598; 242/402; 242/578.1; 242/278.2
(58) Field of Classification Search .......... 242/532.6, 242/578, 578.1, 578.2, 577.4, 399.1, 402, 242/404.2, 588, 598
See application file for complete search history.

(56) References Cited

U.S. PATENT DOCUMENTS

| 329,752 A | * | 11/1885 | Ludlow | ............ 242/472.7 |
| 775,985 A | | 11/1904 | McKain | |
| 1,521,396 A | | 12/1924 | Scott | |
| 2,609,155 A | | 9/1952 | Fosnaugh | |
| 2,671,444 A | | 3/1954 | Pease, Jr. | |
| 3,089,495 A | | 5/1963 | Florio | |
| 3,647,152 A | * | 3/1972 | Trewella | ............ 242/532.6 |
| 3,710,400 A | | 1/1973 | Sparks | |
| 3,998,402 A | * | 12/1976 | Christensen et al. | ......... 242/399 |
| 4,539,716 A | | 9/1985 | Bell | |
| 4,738,740 A | | 4/1988 | Pinchuk | |
| 4,798,606 A | | 1/1989 | Pinchuk | |
| 4,927,410 A | | 5/1990 | Kovacs | |
| 5,176,642 A | | 1/1993 | Clement | |
| 5,203,767 A | | 4/1993 | Cloyd | |
| 5,258,000 A | | 11/1993 | Gianturco | |
| 5,263,969 A | | 11/1993 | Phillips | |
| 5,310,407 A | | 5/1994 | Casale | |
| 5,316,543 A | | 5/1994 | Eberbach | |
| 5,333,624 A | | 8/1994 | Tovey | |
| 5,366,460 A | | 11/1994 | Eberbach | |
| 5,368,602 A | | 11/1994 | de la Torre | |
| 5,397,331 A | | 3/1995 | Himpens et al. | |
| 5,464,403 A | | 11/1995 | Kieturakis et al. | |
| 5,503,623 A | | 4/1996 | Tilton, Jr. | |
| 5,643,317 A | | 7/1997 | Pavcnik et al. | |
| 5,665,067 A | | 9/1997 | Linder et al. | |

(Continued)

FOREIGN PATENT DOCUMENTS

FR  2735015 A1  12/1996

(Continued)

OTHER PUBLICATIONS

International Search Report/Written Opinion for PCT/US2009/067511 (Aug. 3, 2010).

(Continued)

Primary Examiner — William A Rivera

(74) Attorney, Agent, or Firm — Brinks Hofer Gilson & Lione

(57) ABSTRACT

Medical devices and methods are provided for rolling an endoscopic sheet into a tubular configuration.

10 Claims, 4 Drawing Sheets

U.S. PATENT DOCUMENTS

| | | | |
|---|---|---|---|
| 5,695,525 | A | 12/1997 | Mulhauser et al. |
| 5,788,625 | A | 8/1998 | Plouhar et al. |
| 5,873,530 | A | 2/1999 | Chizinsky |
| 5,902,228 | A | 5/1999 | Schulsinger et al. |
| 5,919,184 | A | 7/1999 | Tilton, Jr. |
| 5,947,997 | A | 9/1999 | Pavcnik et al. |
| 5,951,531 | A | 9/1999 | Ferdman et al. |
| 5,972,022 | A | 10/1999 | Huxel |
| 6,007,515 | A | 12/1999 | Epstein et al. |
| 6,021,776 | A | 2/2000 | Allred et al. |
| 6,059,749 | A | 5/2000 | Marx |
| 6,077,217 | A | 6/2000 | Love et al. |
| 6,368,300 | B1 | 4/2002 | Fallon et al. |
| 6,425,900 | B1 | 7/2002 | Knodel et al. |
| 6,551,333 | B2 | 4/2003 | Kuhns et al. |
| 6,610,026 | B2 | 8/2003 | Cragg et al. |
| 6,723,067 | B2 | 4/2004 | Nielson |
| 6,746,458 | B1 | 6/2004 | Cloud |
| 6,811,550 | B2 | 11/2004 | Holland et al. |
| 6,863,660 | B2 | 3/2005 | Marx |
| 7,101,862 | B2 | 9/2006 | Cochrum et al. |
| 7,156,880 | B2 | 1/2007 | Evans et al. |
| 7,485,124 | B2 | 2/2009 | Kuhns et al. |
| 7,641,836 | B2 | 1/2010 | Li et al. |
| 7,670,362 | B2 | 3/2010 | Zergiebel |
| 7,673,783 | B2 | 3/2010 | Morgan et al. |
| 7,753,934 | B2 | 7/2010 | Wilk |
| 7,780,973 | B2 | 8/2010 | Freeman et al. |
| 7,891,063 | B2 * | 2/2011 | Herb-Weinert et al. ........ 28/145 |
| 2001/0034509 | A1 | 10/2001 | Cragg et al. |
| 2003/0181917 | A1 | 9/2003 | Gertner |
| 2003/0216695 | A1 | 11/2003 | Yang |
| 2003/0236573 | A1 | 12/2003 | Evans et al. |
| 2005/0070848 | A1 | 3/2005 | Kim et al. |
| 2005/0171562 | A1 | 8/2005 | Criscuolo et al. |
| 2005/0182445 | A1 | 8/2005 | Zamierowski |
| 2005/0277981 | A1 | 12/2005 | Maahs et al. |
| 2006/0004248 | A1 | 1/2006 | Kute et al. |
| 2008/0048002 | A1 | 2/2008 | Smith et al. |
| 2008/0058710 | A1 | 3/2008 | Wilk |
| 2008/0195121 | A1 | 8/2008 | Eldar et al. |
| 2008/0208219 | A1 | 8/2008 | Suzuki |
| 2009/0234374 | A1 | 9/2009 | Gabel et al. |
| 2009/0234380 | A1 | 9/2009 | Gabel et al. |
| 2009/0248056 | A1 | 10/2009 | Gabel et al. |
| 2010/0042045 | A1 | 2/2010 | Spivey |
| 2010/0049219 | A1 | 2/2010 | Cronin et al. |
| 2010/0087854 | A1 | 4/2010 | Stopek et al. |
| 2010/0137796 | A1 | 6/2010 | Perry et al. |
| 2010/0147990 | A1 | 6/2010 | McLawhorn |
| 2010/0264192 | A1 | 10/2010 | Marczyk |

FOREIGN PATENT DOCUMENTS

| | | | |
|---|---|---|---|
| WO | WO 2004/012627 | A1 | 2/2004 |
| WO | WO 2004/080348 | | 9/2004 |
| WO | WO 2007/090155 | A1 | 8/2007 |

OTHER PUBLICATIONS

International Search Report/Written Opinion for PCT/US09/062066 (Feb. 2, 2010).

Article 34 Amendment for PCT/US09/062066.

* cited by examiner

ENDOSCOPIC SHEET ROLLING SYSTEM

CROSS-REFERENCE TO RELATED APPLICATIONS

This application claims the benefit of U.S. Provisional Application Ser. No. 61/121,794 filed on Dec. 11, 2008, entitled "ENDOSCOPIC SHEET ROLLING SYSTEM" the entire contents of which are incorporated herein by reference.

FIELD

The present application relates generally to endoscopic sheets, and more particularly relates to a rolling system for preparing the endoscopic sheets.

BACKGROUND

Openings or perforations in the walls of internal organs and vessels may be naturally occurring, or formed intentionally or unintentionally. These openings may be used to gain access to adjacent structures of the body, such techniques being commonly referred to as. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many translumenal procedures for gaining access to various body cavities using other bodily lumens have also been developed. Natural orifices such as the mouth, nose, ear, anus or vagina may provide access to such bodily lumens and cavities. The bodily lumen(s) of the gastrointestinal tract are often endoscopically explored and can be utilized to provide access to the peritoneal cavity and other body cavities, all in a minimally invasive manner.

Compared to traditional open surgery or laparoscopic surgery, translumenal procedures are less invasive by eliminating abdominal incisions (or other exterior incisions) and incision related complications, while also reducing postoperative recovery time, reducing pain, and improving cosmetic appearance. At the same time, there remain challenges to translumenal procedures, including providing a suitable conduit to the openings and body cavities, robust medical devices that are maneuverable via the conduit and operable within the body cavity, sterility of the conduit, maintaining insufflation of the body cavity, proper closure of the opening and prevention of infection. These procedures carry the risk of perforating structures that lie just beyond the bodily wall being cut or within the cavity being explored or worked within. For example, when incising the gastric wall, the potential of hitting blood vessels without knowing could lead to bleeding complications.

BRIEF SUMMARY

The present invention provides medical devices and methods for rolling an endoscopic sheet from a flat configuration to a rolled configuration. One embodiment of the device, constructed in accordance with the teachings of the present invention, generally comprises a roller, an elongated base, and first and second fixtures. The roller has a first elongated rod and a second elongated rod, the first and second rods defining a space therebetween sized to receive and edge of the endoscopic sheet. The first fixture is attached to the base and defines a first flange projecting away from the base. The first flange defines a first aperture sized to slidably and rotatably receive the first and second rods. The first and second rods are longitudinally slidable relative to the first fixture, and rotatable relative to the first fixture. The second fixture is also attached to the base and defines a second flange projecting away from the base. The second flange defines a second aperture sized to slidably and rotatably receive the first and second rods. The first and second rods are longitudinally slidable relative to the second fixture, and rotatable relative to the second fixture.

According to more detailed aspects of embodiments of the devices, upon rotation of the roller having an edge of the endoscopic sheet fitted in the space between the first and second rods, the endoscopic sheet is wound around the first and second rods into a tubular configuration. The roller and its first and second rods are longitudinally slidable relative to the tubular endoscopic sheet and the first and second fixtures. The first and second rods preferably have a diameter in the range of about 0.5 mm to about 2.0 mm. The roller may further include a rolling knob attached to adjacent ends of the first and second rods, the adjacent ends being spaced apart a fixed distance. In one embodiment, the first and second apertures in the first and second flanges have a diameter about equal to or less than the diameter of the first rod plus the diameter of the second rod plus a thickness of the endoscopic sheet. In another embodiment, a first bearing is fitted in the first aperture of the first fixture. The first bearing has a pair of bores slidably receiving the first and second rods, and is rotatably mounted within the first aperture of the first fixture. A second bearing may likewise be provided in the second aperture of the second fixture.

According to still further detailed aspects of embodiments of the devices, the first fixture is preferably slidably attached to the base. The first fixture and its first flange are longitudinally slidable relative to the base. A first clamp is connected to the first fixture and selectively fixes the position of the first fixture along the base. The base preferably defines an elongated channel extending therethrough. The first clamp includes a threaded fastener and a clamping plate, the fastener threaded passing through a hole in the first fixture and passing through the channel and threaded through the clamping plate. The second fixture may similarly be slidably attached to the base.

One embodiment of a method of rolling an endoscopic sheet into a tubular configuration, in accordance with the teachings of the present invention, generally comprises the following steps. A rolling device is provided and comprises a roller having a first elongated rod and a second elongated rod, the first and second rods defining a space therebetween sized to receive and edge of the endoscopic sheet, an elongated base, a first fixture and a second fixture attached to the base and defining first and second flanges projecting away from the base, the first and second flanges defining first and second apertures sized to slidably and rotatably receive the first and second rods. An edge of the endoscopic sheet is placed in the space between the first and second rods of the roller. The roller is rotated to wind the endoscopic sheet around the first and second rods into the tubular configuration. The first and second rods are longitudinally slid relative to the tubular endoscopic sheet and the first and second fixtures until the endoscopic sheet is freed from the roller.

According to more detailed aspects of embodiments of the methods, at least one of the first and second fixtures are longitudinally slid relative to the base. The sliding step is preferably performed after the step of placing the endoscopic sheet. The sliding step is preferably performed prior to the step of rotating the roller. The sliding step may be performed after the rolling step and prior to the step of longitudinally sliding the first and second rods. The sliding step preferably places a compressive force on the tubular endoscopic sheet.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION

In the present application, the term "proximal" refers to a direction that is generally towards a physician during a medical procedure, while the term "distal" refers to a direction that is generally towards a target site within a patient's anatomy during a medical procedure.

Figure 1:
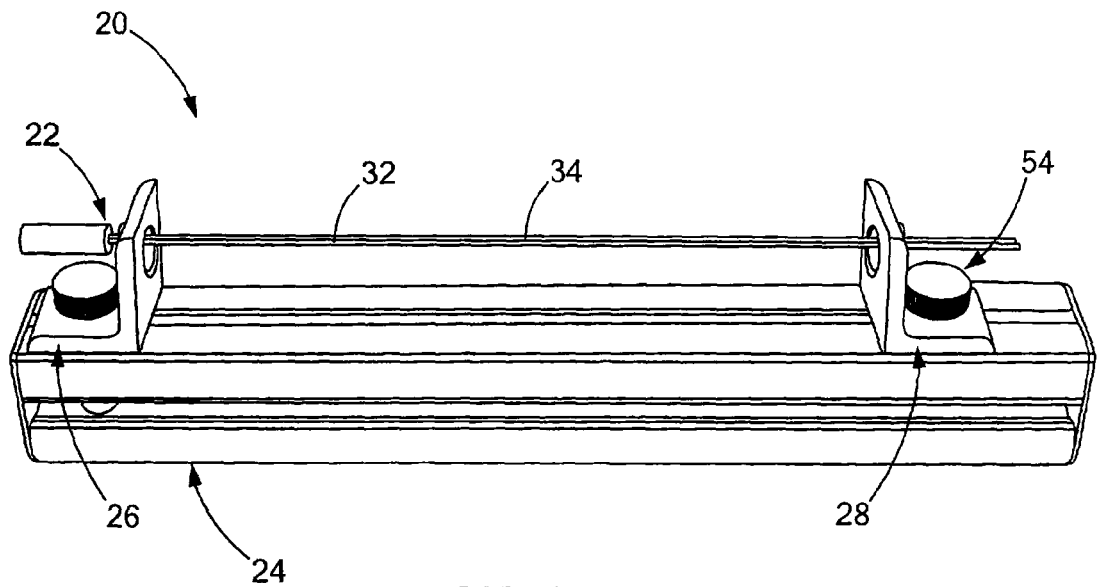
FIG. 1 is a perspective view of a device for rolling an endoscopic sheet constructed in accordance with the teachings of the present invention.
Figure 2:
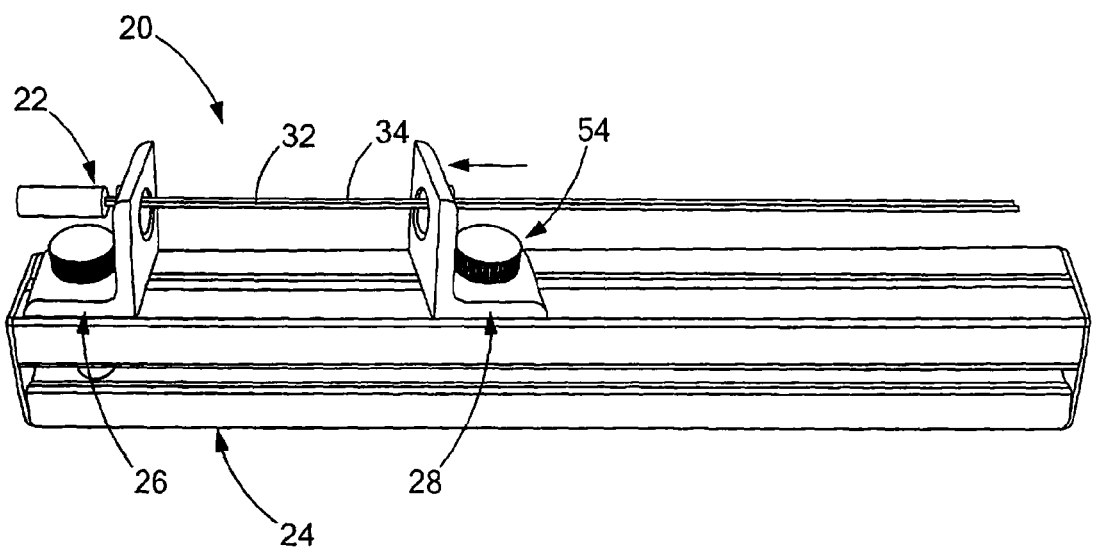
FIG. 2 is another perspective view of the device depicted in FIG. 1.
Figure 10:
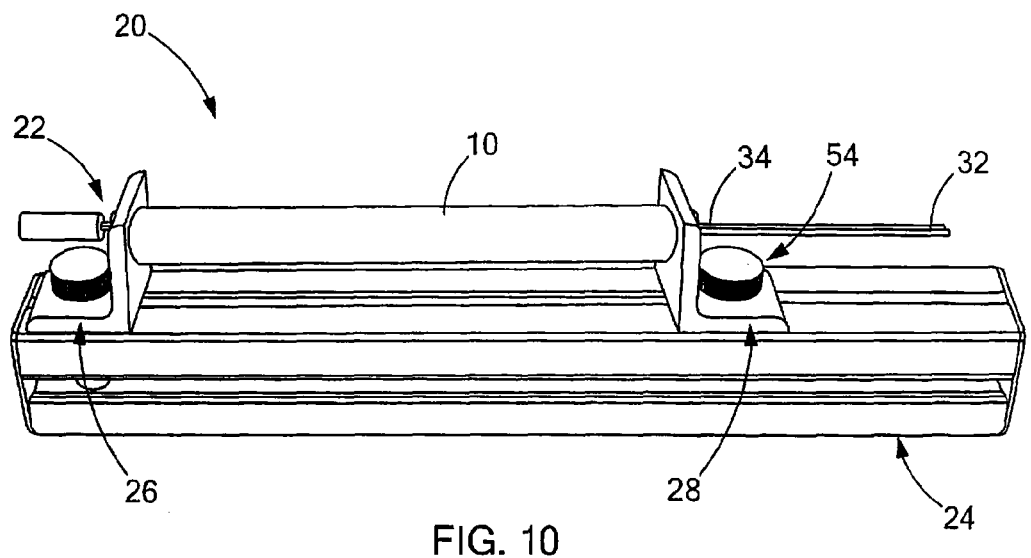

Turning now to the figures, FIGS. 1 and 2 depict a medical device 20 constructed in accordance with the teachings of the present invention. The device 20 generally comprises a roller 22, an elongated base 24 and first and second fixtures 26, 28, respectively. Generally, the roller 22 is utilized to engage and roll an endoscopic sheet 10 (FIG. 8) into a tubular configuration (FIG. 10). To accommodate different sized sheets 10, as well as to improve uniformity to the tubular configuration and assist with sheet rolling, the first and second fixtures 26, 28 are preferably slidable along the base 24, as shown in FIG. 2.

Figure 3:
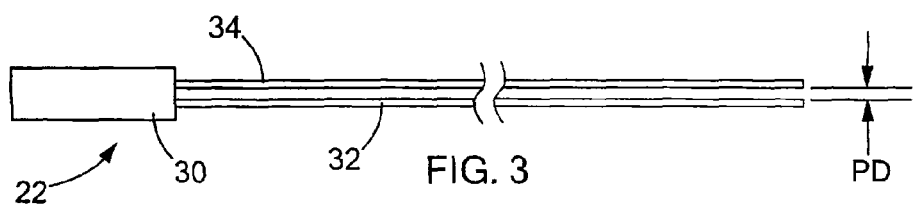
FIG. 3 is a side view of a roller forming a portion of the medical device depicted in FIG. 1.

As shown in FIG. 3, the roller 22 generally comprises a rolling knob 30 attached to adjacent ends of a first rod 32 and a second rod 34. The first and second rods 32, 34 are fixed to the knob 30, and their adjacent ends are spaced apart a predetermined distance PD. The predetermined distance PD is preferably about equal to a thickness of the endoscopic sheet 10. The rods 32, 34 preferably have a rounded cross-section, and most preferably circular cross-section (although this is not necessary) and preferably have an outer diameter about 0.5 mm to about 2.0 mm. The first and second rods 32, 34 may have the same diameter or may have different diameters. The rods may be formed of metal, plastic or ceramics, but preferably are formed from solid metal wire having suitable dimensions (long and thin) for tightly winding a thin endoscopic sheet and functioning as a clamping mandril therefor.

Figure 4:
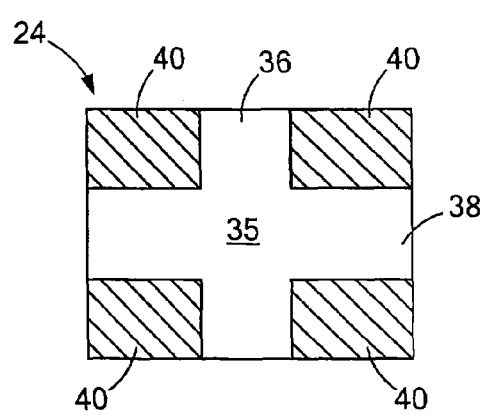
FIG. 4 is a cross-sectional view through a base forming a portion of the device depicted in FIG. 1.
Figure 5:
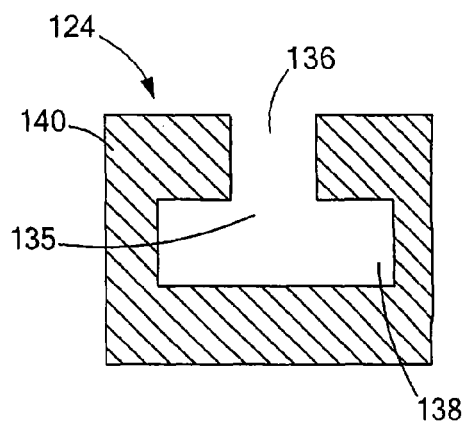
FIG. 5 is a cross-sectional view similar to FIG. 4 but showing another embodiment of the base.

Turning to FIG. 4, the base 24 generally includes elongated bars 40 fitted together as shown via end caps 33 (FIG. 1). The bars 40 may be attached to the end caps 33 by any known means including fasteners, adhesive, bonding, welding, etc. The base 24 defines a channel 35 therein, the channel including a vertical portion 36 and a horizontal portion 38. The channel 35 is used to accommodate the first and second fixtures 26, 28 and their clamps 54 (FIG. 6) for selectively fixing the position of the fixtures 26, 28 along the elongated base 24. One alternate embodiment of the base 124 is shown on FIG. 5. In this embodiment, a unitary bar 140 is formed with an integral channel 135 having a vertical portion 136 and a horizontal portion 138.

Figure 6:
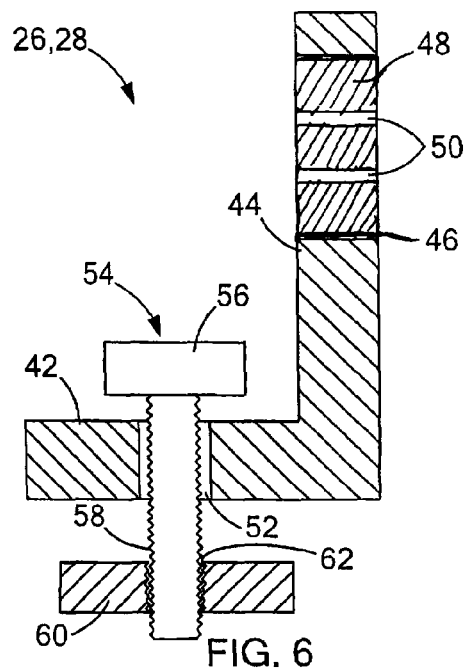
FIG. 6 is a cross-sectional view through a fixture and clamp forming a portion of the device depicted in FIG. 1.

Turning now to FIG. 6, a cross-sectional view of one embodiment of the first and second fixtures 26, 28 is shown. Generally, the first and second fixtures 26, 28 are identically formed, although this is not necessary and in fact it may be desirable to modify one of the fixtures depending upon the particular application and structure of the endoscopic sheet 10. The fixture 26, 28 generally comprises a horizontal slide 42 connected to a vertical flange 44. The flange 44 projects away from the slide 42, and as best seen in FIG. 1, projects away from the elongated base 24. The slide 42 is adapted to ride along an upper surface of the elongated base 24. The flange 44 defines an aperture 46 received a bearing 48 therein. The bearing 48 is rotatably mounted within the aperture 46, and their mating surfaces may include suitable lubricants or friction-reducing coatings. The bearing 48 further includes a pair of bores 50 slidably receiving the first and second rods 32, 34 of the roller 22. The rods 32, 34 are longitudinally translatable relative to the fixtures 26, 28 via the bores 50.

The fixture 26, 28 preferably further includes a clamp 54 for selectively fixing the location of the fixture 26, 28 along the elongated base 24. The clamp 54 includes a control knob 56 attached to a threaded fastener 58. The threaded fastener 58 passes through a hole 52 in the slide 42 of the fixture 26, 28. The fastener 58 is threadingly engaged with a clamping plate 60 via its threaded bore 62. The clamping plate 60 is rectangular or oblong, or otherwise structured to be mounted within the channel 35 of the elongated base 24 so that it cannot rotate horizontally. Accordingly, upon affecting rotation of the threaded fastener 58 via the control knob 56, the fastener 58 rotates relative to the clamping plate 60 and causes it to move vertically therealong. As such, the clamp 54 may be used to selectively fix the location of the fixture 26, 28 along the elongated base 24.

Figure 7:
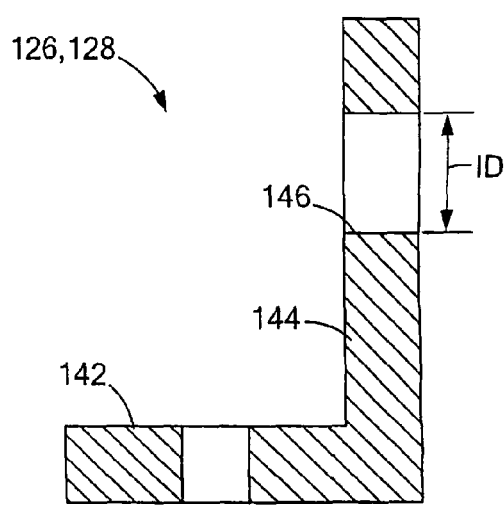
FIG. 7 is a cross-sectional view similar to FIG. 6, showing an alternate embodiment of the flange.

Another embodiment of a fixture 126, 128 is depicted in FIG. 7. As with the previous embodiment, the fixture 126, 128 includes a slide 142 and a flange 144. In this embodiment, the flange 134 defines an aperture 146 that does not include a bearing 48. An inner diameter ID of the aperture 146 is preferably sized to be about equal to the sum of the diameters of the first and second rods 32, 34 and the predetermined distance PD which they are spaced apart. Alternatively, the aperture 146 has an inner diameter ID sized to be about equal to the sum of the diameters of the first and second rods 32, 34 and a thickness of the endoscopic sheet 10. The aperture 146 is generally sized and structured to permit rotation of the rods 32, 34 therein while having the endoscopic sheet 38 positioned therebetween. The aperture 146 may be lined with a friction-reducing coating or other materials.

Figure 8:
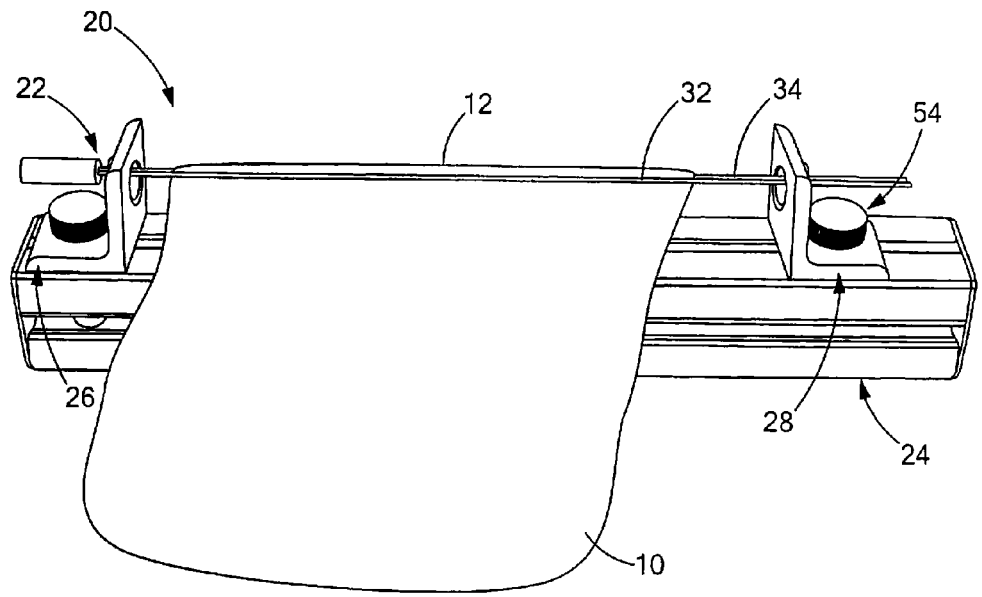
FIGS. 8-11 are perspective views of the medical device depicted in FIG. 1, showing a method of rolling an endoscopic sheet.
Figure 9:
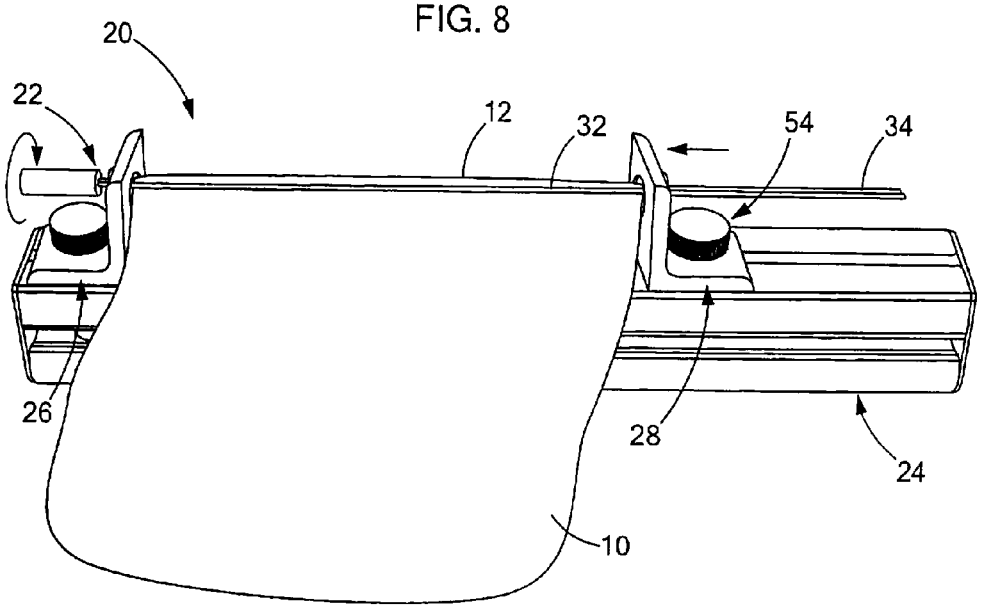
Figure 11:
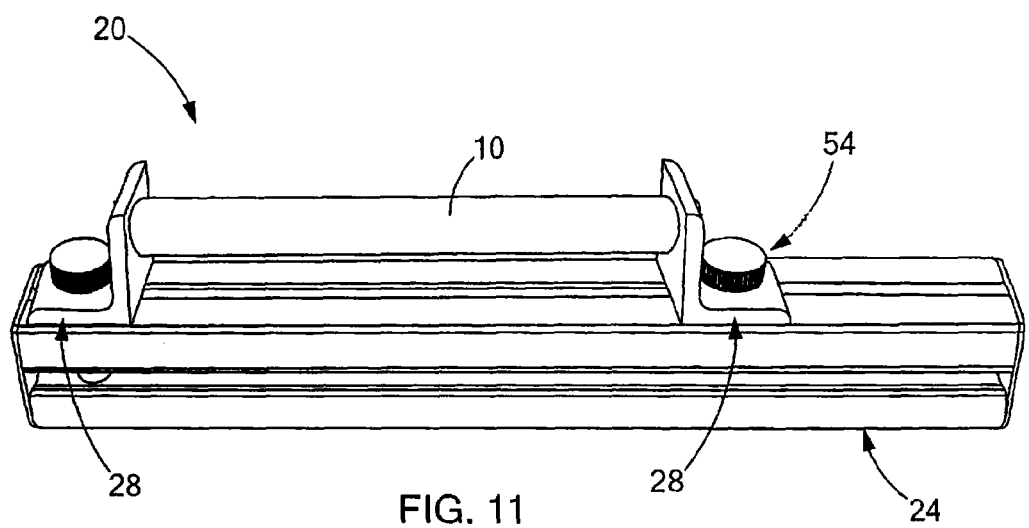

Turning now to FIGS. 8-11, a method of using the device 22 roll and endoscopic sheet 10 will now be described. One embodiment of the rolling device 20 is provided, and an edge 12 of the endoscopic sheet 10 is placed in the space between the first and second rods 32, 34 of the roller 22. The first and second fixtures 26, 28 may be appropriately slid longitudinally relative to the base 24 to accommodate the endoscopic sheet 10, while providing a guiding surface to the side edges of the sheet 10 during the rolling process, as shown in FIG. 9. The roller 22 is rotated to wind the endoscopic sheet 10 around the first and second rods 32, 34 and into a tubular configuration, shown in FIG. 10. Optionally, the one or both of the fixtures 26, 28 may be again slid longitudinally to place a compressive force on the tubular endoscopic sheet 10, or to reduce a compressive force on the tubular endoscopic sheet 10. As shown in FIG. 11, the first and second rods 32, 34 of the roller 22 are slid longitudinally relative to the tubular endoscopic sheet 10 (as well as relative to the first and second fixtures 26, 28) until the tubular endoscopic sheet is freed from the roller. If desired, the fixtures 26, 28 may again be slid longitudinally as desired.

Accordingly, it can be seen that the devices and methods of the present application depict a robust and vertical apparatus for rolling an endoscopic sheet quickly and efficiently. Exemplary uses tubular endoscopic sheets are disclosed in copending U.S. patent application Ser. No. 12/605,794 filed Oct. 26, 2009, the entire disclosure of which is hereby incorporated by reference in its entirety.

The sheet 10 is preferably formed of a various materials, including knitted, woven or non-woven fabrics, gauze, meshes, sponge sheets, foam sheets, plastic sheets, tissue layers and ECM materials. Synthetic materials may also be used, e.g. PIFE, polypropylene, and polyester fabrics or meshes and the like. The sheet 10 may have many different forms and shapes such a round, square, rectangular, triangular, etc. A generally rectangular sheet 10 is shown in FIG. 8, and preferably has a width between about 1 cm to about 5 cm, a length of about 2 cm to about 15 cm, and a thickness between about 0.1 mm to about 1.2 mm. Most preferably the sheet 10 is about 2 cm by wide by about 8 cm long, and 0.3 mm thick.

One preferred class of materials formed as sheets include extracellular matrix (ECM) materials. For example, the sheet 10 may comprise small intestinal submucosa (SIS), such those sold under the trademarks SURGISIS BIODESIGN®, available from Cook Medical Inc., of Bloomington, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. Preferably, the sheet 24 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The sheet 24 may also comprise a composite of a biomaterial and a biodegradeable polymer. Additional details may be found in U.S. Pat. No. 6,206,931 to Cook et al., the disclosure of which is incorporated herein by reference in its entirety.

Additionally, the ECM material of the invention can be subjected to processes that expands the material. In certain forms, such expanded material can be formed by the contacting the ECM material with one or more alkaline substances until the material expands. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner. Illustratively, the expanded material can be enriched with bioactive components, dried, and/or molded, etc., in the formation of a sheet of a desired shape or configuration. In certain embodiments, an expanded ECM material construct an be highly compressible and expandable such that the material can be compressed for delivery, such as from within the lumen of a cannulated delivery device, and thereafter expand upon deployment from the device so as to become anchored within a patient, cause closure of a tract within the patient, and/or cause hemostasis. Further details may be found in U.S. patent application Ser. Nos. 12/488,974 filed Jun. 22, 2009, 12/488,996 filed Jun. 22, 2009, and 12/489,199 filed Jun. 22, 2009, and PCT/US2009/04907 filed Jun. 29, 2009, the disclosures of which are hereby incorporated by reference in their entirety.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A device for rolling an endoscopic sheet from a flat configuration to a rolled configuration, the device comprising:
    a roller having a first elongated rod and a second elongated rod, the first and second rods defining a space therebetween sized to receive and edge of the endoscopic sheet;
    an elongated base;
    a first fixture attached to the base and defining a first flange projecting away from the base, the first flange defining a first aperture sized to slidably and rotatably receive the first and second rods, the first and second rods longitudinally slidable relative to the first fixture, the first and second rods rotatable relative to the first fixture;
    a second fixture attached to the base and defining a second flange projecting away from the base, the second flange defining a second aperture sized to slidably and rotatably receive the first and second rods, the first and second rods longitudinally slidable relative to the second fixture, the first and second rods rotatable relative to the second fixture; and
    wherein the first fixture is slidably attached to the base, the first fixture and its first flange being longitudinally slidable relative to the base, and further comprising a first clamp connected to the first fixture and selectively fixing the position of the first fixture along the base, wherein the base defines an elongated channel extending therethrough, and wherein the first clamp includes a threaded fastener and a clamping plate, the fastener threaded through a hole in the first fixture and passing through the channel and threaded through the clamping plate.

2. The device of claim 1, wherein the first and second rods have a diameter in the range of about 0.5 mm to about 2.0 mm.

3. The device of claim 1, wherein the roller further includes a rolling knob attached to adjacent ends of the first and second rods, the adjacent ends being spaced apart a fixed distance.

4. The device of claim 1, wherein the first and second apertures in the first and second flanges have a diameter about equal to or less than the diameter of the first rod plus the diameter of the second rod plus a thickness of the endoscopic sheet.

5. The device of claim 1, wherein the first fixture and the second fixture are slidably attached to the base, the first fixture and its first flange being longitudinally slidable relative to the base, the second fixture and its second flange being longitudinally slidable relative to the base.

6. The device of claim 1, further comprising a first bearing fitted in the first aperture of the first fixture, the first bearing having a pair of bores slidably receiving the first and second rods, the first bearing rotatably mounted within the first aperture of the first fixture.

7. The device of claim 6, further comprising a second bearing fitted in the second aperture of the second fixture, the second bearing having a pair of bores slidably receiving the first and second rods, the second bearing rotatably mounted within the second aperture of the second fixture.

8. The device of claim 1, whereupon rotation of the roller having an edge of the endoscopic sheet fitted in the space between the first and second rods, the endoscopic sheet is wound around the first and second rods into a tubular configuration.

9. The device of claim 8, wherein the roller and its first and second rods are longitudinally slidable relative to the tubular endoscopic sheet and the first and second fixtures.

10. The device of claim 1, wherein the first and second rods are formed from metal wire.

* * * * *